(12) United States Patent
Deshpande et al.

(10) Patent No.: US 6,919,449 B2
(45) Date of Patent: Jul. 19, 2005

(54) PROCESS FOR THE PREPARATION OF CEPHALOSPORIN INTERMEDIATE AND ITS USE FOR THE MANUFACTURE OF CEPHALOSPORIN COMPOUNDS

(75) Inventors: Pandurang Balwant Deshpande, Maharashtra (IN); Parven Kumar Luthra, Chennai (IN); Pratik Ramesh Sathe, Chennai (IN); Sivakumaran Sundaravadivelan, Kanchipuram (IN); Praveen Nagesh Ganesh, Chennai (IN)

(73) Assignee: Orchid Chemicals and Pharmaceuticals Limited, Tamilnadu (IN)

( * ) Notice: Subject to any disclaimer, the term of this patent is extended or adjusted under 35 U.S.C. 154(b) by 180 days.

(21) Appl. No.: 10/245,490

(22) Filed: Sep. 18, 2002

(65) Prior Publication Data
US 2003/0199712 A1 Oct. 23, 2003

(30) Foreign Application Priority Data
Apr. 19, 2002 (IN) .................................... 305/MAS/2002

(51) Int. Cl.[7] .................... C07D 501/36; C07D 501/46; C07D 501/24; A61K 31/546; A61P 31/04
(52) U.S. Cl. ...................... 540/222; 544/225; 544/227; 544/228; 560/168
(58) Field of Search ................... 540/222, 225, 540/227, 228

(56) References Cited

U.S. PATENT DOCUMENTS 4,933,486 A * 6/1990 Ritter et al. ................ 560/168
5,109,131 A * 4/1992 Naito et al. ................. 540/227
2004/0054224 A1 * 3/2004 Kansal et al. ............... 562/560

FOREIGN PATENT DOCUMENTS

| EP | 0 030 294 A2 | 11/1980 | |
|---|---|---|---|
| EP | 416857 A2 * | 3/1991 | ......... C07C/249/12 |
| EP | 0 842 937 A2 | 5/1998 | |

* cited by examiner

*Primary Examiner*—Mark L. Berch
(74) *Attorney, Agent, or Firm*—Oliff & Berridge, PLC

(57) ABSTRACT

The present invention relates to a method for the preparation of cephalosporin antibiotic of the formula (II), which comprises hydrolyzing and halogenating the ester of formula (III)

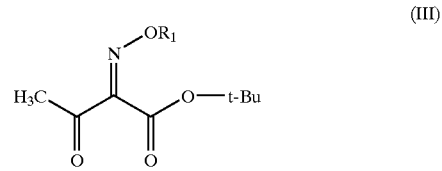

by photochemical irradiation in one pot using a halogenating agent in the absence or presence of a solvent, to produce compound of formula (I), activating the 4-halogeno-2-substitutedimino-3-oxo-butyric acid of formula (I) using conventional activation agents gives compound of formula (IV), condensing the activated compound of the formula (IV) with 7-amino cephem derivative of the formula (V) to produce a compound of formula (VI), and cyclizing the compound of formula (VI) with thiourea to give cephalosporin compounds of the formula (II).

15 Claims, No Drawings

PROCESS FOR THE PREPARATION OF CEPHALOSPORIN INTERMEDIATE AND ITS USE FOR THE MANUFACTURE OF CEPHALOSPORIN COMPOUNDS

FIELD OF INVENTION

The present invention relates to a process for the preparation of 4-halogeno-2-substituted imino-3-oxo-butyric acid of general formula (I)

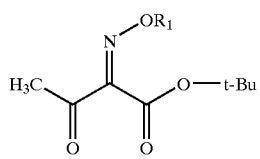

wherein $R_1$ represents $CH_3$, $CR^aR^bCOOR^c$ where $R^a$ and $R^b$ independently represent hydrogen or methyl and $R^c$ represents hydrogen or $(C_1$–$C_6)$alkyl; X represents halogen such as chlorine or bromine.

The invention also discloses the activation of this acid and its further use in the preparation of cephalosporin antibiotic of formula (II) or its solvates in excellent yields and purity.

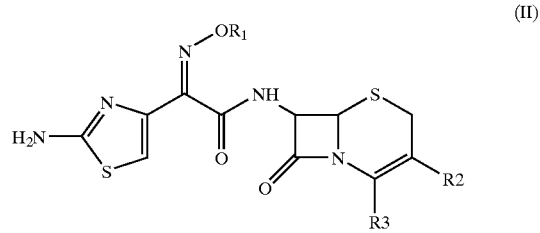

wherein $R_1$ represents $CH_3$, $CR^aR^bCOOR^c$ where $R^a$ and $R^b$ independently represent hydrogen or methyl and $R^c$ represents hydrogen or $(C_1$–$C_6)$alkyl; $R_2$ represents H, $CH_3$, $CH_2OCH_3$, $CH_2OCOCH_3$, $CH=CH_2$,

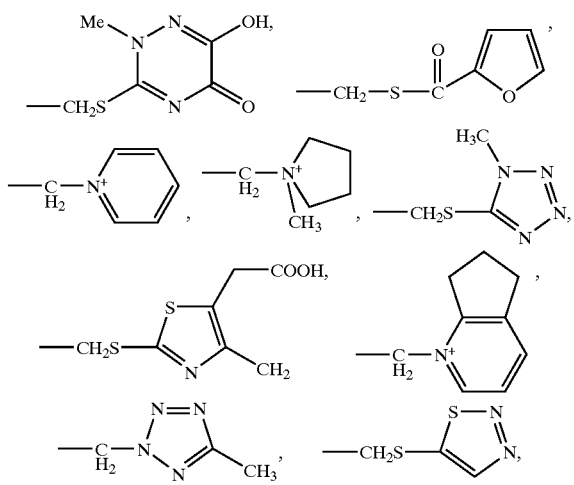

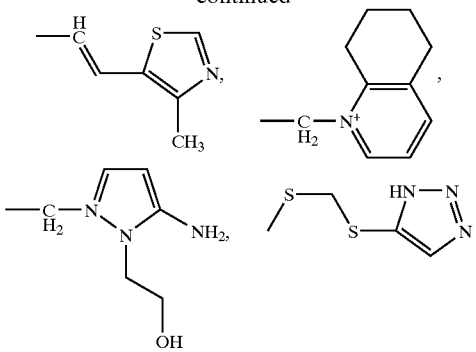

$R_3$ is carboxylate ion or $COOR^d$, where $R^d$ represents hydrogen, esters which form a prodrug or a counter ion which forms a salt.

BACKGROUND OF THE INVENTION

U.S. Pat. No. 5,095,149 describes a process for the preparation of 4-halogeno-2-methoxyimino-3-oxo-butyric acid of formula (I) by brominating the methoxy imino compound of general formula (III) by bromine in mixture of IPE and ethylene dichloride. Ethylene dichloride is a toxic solvent and hence its use in the preparation of pharmaceuticals has to be avoided.

U.S. Pat. No. 5,109,131 describes a process for the preparation of 4-halogeno-2-methoxyimino-3-oxo-butyric acid of formula (I) starting with the reaction of diketene and, tert-butyl alcohol, followed by oximation, methylation, hydrolysis and halogenation. This method involves the hydrolysis and halogenation in two steps.

Synthesis of 4-halogeno-2-methoxyimino-3-oxo-butyric acid is reported in patent no. EP 0 030 294 and a large number of references are available in the patent literature disclosing the use of 4-halogeno-2-substituted imino-3-oxo-butyric acid represented by formula (I) as the starting material. EP 0030294 discloses the condensation of the 4-halogeno-2-substituted imino-3-oxo-butyric acid represented by formula (I) with cephem carboxylic acids by using $PCl_5$. Another EP patent 0 842 937 discloses the formation of amide bond with cephem moiety by reacting with the thioester derivative of 4-chloro-2-methoxyimino-3-oxo-butyric acid. The thioester was prepared by reacting 4-chloro-2-methoxyimino-3-oxo-butyric acid with 2,2'-dithio-bis-benzothiazole in the presence of triphenyl phosphine which is a costly material and its by product triphenyl phosphine oxide is also difficult to remove from the reaction mixture.

OBJECTIVES OF THE INVENTION

The primary objective of the invention is to provide a new process for the preparation of 4-halogeno-2-substituted imino-3-oxo-butyric acid of the general formula (I), which would be suitable for being used in the manufacture of cephalosporin antibiotic, which would be easy to implement in commercial scales.

Another objective of the present invention is to provide a process for the preparation of 4-halogeno-2-substituted imino-3-oxo-butyric acid of the general formula (I), in good yields with high purity.

Another objective of the present invention is to carry out the halogenation by photochemical irradiation which would give higher yield and halogenation can also be achieved in

3 presence or absence of solvents thus making the process more environmental friendly.

Another objective of the present invention is to provide a process for the preparation of cephalosporin antibiotics e.g. cefotaxime, ceftriaxone, cefetamet, ceftiofur, cefditoren, cefpodoxime, ceftadizime, cefepime, cefixime, cefinenoxime, cefodizime, cefoselis, cefquinome, cefpirome, cefteram, cefuzonam etc. which comprises use of 4-halogeno-2-substituted imino-3-oxo-butyric acid of the general formula (I), prepared by the process of the present invention.

SUMMARY OF THE INVENTION

Accordingly, the present invention provides a process for the preparation of 4-halogeno-2-substituted imino-3-oxo-butyric acid of formula (I), which comprises hydrolysis and halogenation of the ester of formula (III) by photochemical irradiation in one pot using a halogenating agent in the absence or presence of a solvent at a temperature in the range of −20° C. to 30° C. The reaction is as shown in the Scheme-1 below:

Scheme-1

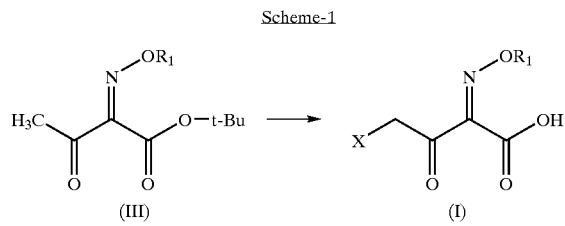

wherein $R_1$ represents $CH_3$, $CR^aR^bCOOR^c$ where $R^a$ and $R^b$ independently represent hydrogen or methyl and $R^c$ represents hydrogen or $(C_1–C_6)$alkyl; X represents halogen such as chlorine or bromine.

4

DETAILED DESCRIPTION OF THE INVENTION

In an embodiment of the present invention relates to a process for the condensation of the acid of formula (I) thus produced with different 7-amino cephem derivatives of formula (V), which comprises:

(i) activation of the 4-halogeno-2-substitutedimino-3-oxo-butyric acid of general formula (I), using conventional activation agents at a temperature in the range of −50° C. to 10° C. to produce a compound formula (IV) where $R_1$ and X are as defined above and X' represents halogen such as chlorine, bromine or activating groups such as

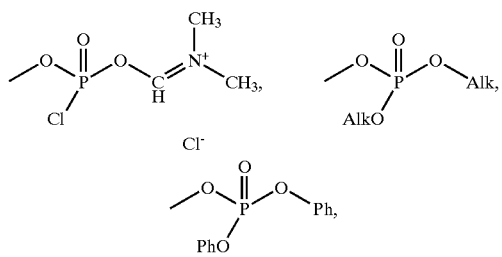

where Alk group represents $(C_1–C_4)$alkyl group such as methyl, ethyl, n-propyl, iso-propyl, n-butyl or iso-butyl.

(iii) condensing the activated compound of formula (IV) with 7-amino cephem derivatives of formula (V) where $R_4$ is hydrogen or trimethylsilyl, $R_2$ and $R_3$ are as defined earlier, in the presence of a solvent at a temperature in the range of −50° C. to 10° C. to produce an active compound of formula (VI) where all symbols are as defined earlier, (iv) cyclising the compound of formula (VI) with thiourea in the presence of water miscible solvents to produce cephalosporin antibiotic of formula (II), where all symbols are as defined earlier, and (v) optionally converting the compound of formula (II) to its pharmaceutically acceptable esters, salts or solvates.

The process is as shown in scheme-2 below:

Scheme-2

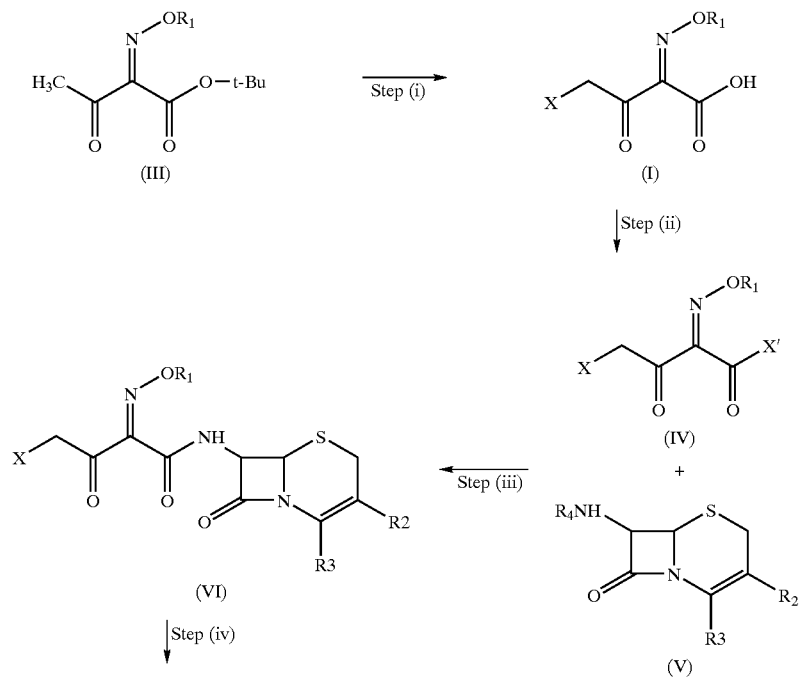

-continued

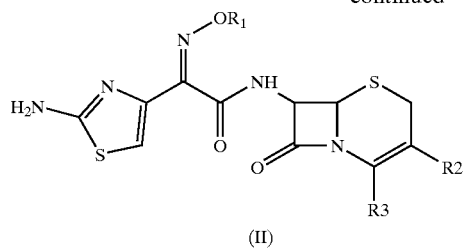

(II)

Another embodiment of the present invention, the compound of formula (VI) can be cyclised with the thiourea without isolating the condensed product.

In yet another embodiment of the present invention there is provided a novel intermediate of formula (IV)

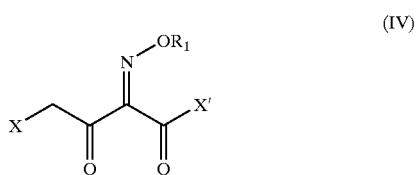

(IV)

wherein X represents halogen such as chlorine or bromine, $R_1$ represents $CH_3$, $CR^aR^bCOOR^c$ where $R^a$ and $R^b$ independently represent hydrogen or methyl and $R^c$ represents hydrogen or $(C_1-C_6)$alkyl and X' represents an activating group such as

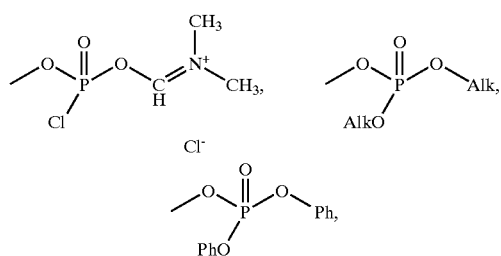

where Alk group represents $(C_1-C_4)$alkyl group such as methyl, ethyl, n-propyl, iso-propyl, n-butyl or iso-butyl.

In another embodiment of the present invention, the solvent used in step (i) is selected from diisopropyl ether, dichloromethane, acetic acid and mixtures thereof. The halogenating agent used is chlorine or bromine.

In yet another embodiment of the present invention, provides a process to perform bromination by photochemical irradiation in the absence or presence of a solvent.

In yet another embodiment of the present invention, the light source used for photochemical halogenation is IR or UV radiation, preferably UV radiation.

In still another embodiment of the present invention, the activation in step (ii) is carried out using $PCl_5$, $DMF/POCl_3$, oxalyl chloride, $SOCl_2/DMF$, diphenylchlorophosphoridate, dialkyl chlorophosphoridate, in the presence of a solvent selected from halogenated alkanes, ethyl acetate, tetrahydrofuran, aromatic hydrocarbons, acetone, acetonitrile, dialkylethers or mixtures thereof.

In yet another embodiment of the present invention condensation in step (iii) is carried out in the presence of a solvent selected from halogenated alkanes, ethyl acetate, tetrahydrofuran, aromatic hydrocarbons, acetone, acetonitrile, dialkylethers or mixtures thereof.

In yet another embodiment of the present invention the cyclisation in step (iv) is carried out using a mixture of water and organic solvent selected from tetrahydrofuran, acetone, acetonitrile, N,N-dimethylformamide, N,N-dimethylacetamide, dioxane, $(C_1-C_3)$ alcohol or mixtures thereof, in the presence of sodium acetate.

In still another embodiment of the present invention the counter ion represented by $R^d$ is alkali metal, preferably sodium.

In still another embodiment of the present invention the prodrug ester represented by $R^d$ is —$(CH_2)$—O—C(=O)—C(CH_3)_3$, —CH(CH_3)$—O—C(=O)—CH_3$ or —CH$(CH_3)$—O—C(=O)—O—CH(CH_3)_2$.

In another embodiment of the present invention the compound of formula (I) obtained is a syn-isomer.

In another embodiment of the present invention, the compound of formula (V), when $R_4$ represents trimethylsilyl, the silylation is carried out by using silylating agent selected from N,O-bis-(trimethylsilyl)acetamide (BSA), hexamethyldisilazane (HMDS) trimethylchlorosilane (TMCS), dichlorodimethylsilane.

Many other beneficial results can be obtained by applying disclosed invention in a different manner or by modifying the invention with the scope of disclosure. However, since the major characteristic feature of the present invention resides in the preparation of 4-halogeno-2-substituted imino-3-oxo-butyric acid of general formula (I) in preparing the cephalosporin antibiotics, the technical scope of the present invention should not be limited to the following examples.

The following examples are provided by way of illustration only and should not be limited to construe the scope of the invention

EXAMPLE—1

Preparation of 4-chloro-2-methoxyimino-3-oxobutyric Acid Using Photochemical Irradiation In di-isopropyl ether (250 ml), tert-butyl 2-methoxyimino-3-oxobutyrate (100 gm) was dissolved and chlorine gas was introduced into the solution at 0–5° C. in the presence of ultraviolet radiation over a period of 18 hours. After completion of the introduction, water (150 ml) was added and then stirred to conduct the water washing to remove the inorganic by-products.

Subsequently the organic layer was dried over anhydrous magnesium sulphate, after which the solvent was distilled off under reduced pressure. To the residual was added xylene (100 ml), cooled to (−5 to −10° C.) to get the white crystals of 4-chloro-2-methoxyimino-3-oxobutyric acid. (Purity: 96–98%)

EXAMPLE—2

Preparation of 4-chloro-2-methoxyimino-3-oxobutyric Acid Using Photochemical Irradiation t-Butyl 2-methoxyimino-3-oxobutyrate (100 g) was taken in the reactor and chlorine gas was introduced into the solution at 10–20° C. in the presence of ultraviolet radiation over a period of 18 hours. After completion of the introduction, water (150 ml) was added and then stirred to conduct the water washing to remove the inorganic by-products.

Subsequently the product was dried over anhydrous magnesium sulphate and decanted. Vacuum was applied to pull out traces of acidic vapors. To the residue was added xylene (100 ml), cooled to (−5 to −10° C.) to get the white crystals of 4-chloro-2-methoxyimino-3-oxobutyric acid. (Purity: 96–98%)

EXAMPLE—3

Preparation of 7-[[(Z)-2-(aminothiazol-4-yl)-2-methoxyimino]acetamido]-3-(furanylcarbonyl)thiomethyl]-3-cephem-4-carboxylic Acid Sodium (Ceftiofur Sodium).

Step—I
Silylation of 7-amino-3-[(2-furanylcarbonyl)thiomethyl]-3-cephem-4-carboxylic Acid:

Methylene dichloride (100 ml) was charged to the reaction flask followed by addition of 7-amino-3-[(2-furanylcarbonyl)thiomethyl]-3-cephem-4-carboxylic acid (10.0 g) and stirred at room temperature. N, O-bis-(trimethylsilyl)acetamide (BSA) (18.0 g) was added drop wise at room temperature and continued stirring for 2–3 hrs at the same temperature.

Step—II
Activation of 4-chloro-2-methoxyimino-3-oxobutyric Acid with $PCl_5$

Methylene dichloride (60 ml) was charged in the flask followed by addition of 4-chloro-2-methoxyimino-3-oxobutyric acid (6.3 g) obtained in example 1 or 2 and stirred at −40° C. $PCl_5$ (7.3 g) was added portion wise at −40° C. and continued stirring for 1 hr at the same temperature.

Step—III
Condensation of Activated 4-chloro-2-methoxyimino-3-oxobutyric Acid and Silylated 7-amino-3-[(2-furanylcarbonyl)thiomethyl]-3-cephem-4-carboxylic Acid Silylated 7-amino-3-[(2-furanylcarbonyl)thiomethyl)-3-cephem-4-carboxylic acid obtained in step (I) above, at −40° C. was transferred to the activated 4-chloro-2-methoxyimino-3-oxobutyric acid obtained in step (II) above, in one lot. The temperature of the reaction mass was maintained at −40° C. for 30 min. The progress of the reaction was monitored by HPLC. After completion of the reaction, water (100 ml) was added, stirred at room temperature for another 30 min. The precipitated product was filtered and washed with water to give the condensed product (Purity 99.0%).

Step (IV)
Cyclisation with Thiourea

Tetrahydrofuran (150 ml) and water (75 ml) were charged into the reaction flask followed by the addition of condensed product (15.0 g) obtained in step (III) above, thiourea(2.7 g) and sodium acetate (8.0 g). Stirred the reaction mixture at room temperature for 3 hrs. The progress of the reaction was monitored by HPLC. After completion of reaction, sodium chloride (145.0 g) was added to the reaction mixture and stirred at room temperature for 30 min. The tetrahydrofuran layer was separated and was added THF (240 ml), charcoal (5.0 g) stirred for 1 hr at room temperature. To the THF layer $MgSO_4$ (15.0 g) was added to remove the traces of water, decanted the THF layer, to which sodium-2-ethyl hexanoate (9.4 g, 168 mw) in THF (50 ml) was added. Precipitation of the product started after 1 hr of stirring. The precipitated ceftiofur sodium was filtered and washed with acetone (11.0 g, Purity 99.0%).

EXAMPLE—4

Preparation of 7-[[(Z)-2-(aminothiazol-4-yl)-2-methoxyimino]acetamido]-3-[(2,5-dihydro-6-hydroxy-2-methyl-5-oxo-1,2,4-triazin-3-yl)thiomethyl]-3-cephem-4-carboxylic Acid Sodium (Ceftriaxone Sodium).

Step—I
Silylation of 7-amino-3-[(2,5-dihydro-6-hydroxy-2-methyl-5-oxo-1,2,4-triazin-3-yl)thiomethyl]-3-cephem-4-carboxylic Acid:

Methylene dichloride (70 ml) was charged to the reaction flask followed by addition of 7-amino-3-[(2,5-dihydro-6-hydroxy-2-methyl-5-oxo-1,2,4-triazin-3-yl)thiomethyl]-3-cephem-4-carboxylic acid (5.0 g, 1.0 mol) and stirred at room temperature. N, O-bis-(trimethylsilyl)acetamide (BSA) (9.0 g, 3.3 mol) was added drop wise at room temperature and continued stirring for 2–3 hrs at the same temperature. The mixture was then cooled to −30° C.

Step—II
Activation of 4-chloro-2-methoxyimino-3-oxo-butyric Acid with $PCl_5$

Methylene dichloride (20 ml) was charged in the flask followed by addition of 4-chloro-2-methoxyimino-3-oxobutyric acid (2.6 g, 1.1 mol) obtained in example 1 or 2 and stirred at −30° C. $PCl_5$ (3.3 g, 1.1 mol) was added portion wise at −30° C. and continued stirring for 1 hr at the same temperature.

Step—III
Condensation of Activated 4-chloro-2-methoxyimino-3-oxo-butyric Acid and Silylated 7-amino-3-[(2,5-dihydro-6-hydroxy-2-methyl-5-oxo-1,2,4-triazin-3-yl) thiomethyl]-3-cephem-4-carboxylic Acid Silylated 7-amino-3-[(2,5-dihydro-6-hydroxy-2-methyl-5-oxo-1,2,4-triazin-3-yl)thiomethyl]-3-cephem-4-carboxylic acid obtained in step (I) above, at −30° C. was transferred to the activated 4-chloro-2-methoxyimino-3-oxobutyric acid obtained in step (II) above, in one lot. The temperature of the reaction mass was maintained at −30° C. for 30 min. The progress of the reaction was monitored by HPLC. After completion of the reaction, the reaction mixture was poured into chilled DM water (200 ml), stirred at room temperature for another 1 hour. The precipitated product was filtered and washed with water to give the condensed product (Purity 99.0%).

Step (IV)
Cyclisation with Thiourea

To a mixture of 50 ml THF and 50 ml DM water was added the condensed compound (10.0 gm, 1.0 mol) obtained in step (III) above, followed by thiourea (2.85 gm, 2.0 mol) and sodium acetate (7.7 gm, 5.0 mol). The reaction was stirred for 1.0 hour at room temperature. After completion of reaction, the mixture was cooled to 0° C. and adjusted to pH 3.0 with 1:1 HCl. The precipitated solid was filtered, washed with DM water and the wet solid was charged into a mixture of acetone (300 ml) and DM water (30 ml). The reaction mass was cooled to 0° C. and pH adjusted to 6.8 with saturated sodium acetate and stirred for 30 minutes. The precipitated solid was filtered, washed with 2×30 ml chilled acetone and dried under nitrogen to yield Ceftriaxone sodium salt.(Purity: 99%).

EXAMPLE—5

Preparation of 7-[[(Z)-2-(aminothiazol-4-yl)-2-methoxyimino]acetamido]-3-acetoxymethyl]-3-cephem-4-carboxylic Acid (Cefotaxime).

Step—I

Silylation of 7-amino-3-acetoxymethyl-3-cephem-4-carboxylic Acid:

Methylene dichloride (140 ml) was charged to the reaction flask followed by addition of 7-amino-3-acetoxymethyl-3-cephem-4-carboxylic acid (10.0 gm, 1.0 mol) and stirred at room temperature. N, O-bis-(trimethylsilyl)acetamide (BSA) (24.6 g, 3.3 mol) was added drop wise at room temperature and continued stirring for 3 hrs at the same temperature to get a clear solution. The mixture was cooled to −30° C.

Step—II

Activation of 4-chloro-2-methoxyimino-3-oxobutyric Acid with $PCl_5$

Methylene dichloride (30 ml) was charged in the flask followed by addition of 4-chloro-2-methoxyimino-3-oxobutyric acid (7.2 gm, 1.1 mol) obtained in example 1 or 2 and stirred at −30° C. $PCl_5$ (9.3 gm, 1.1 mol) was added portion wise at −30° C. and continued stirring for 1 hr at the same temperature.

Step—III

Condensation of Activated 4-chloro-2-methoxyimino-3-oxobutyric Acid and Silylated 7-amino-3-acetoxymethyl-3-cephem-4-carboxylic Acid Silylated 7-amino-3-acetoxymethyl-3-cephem-4-carboxylic acid obtained in step (I) above at −30° C. was transferred to the activated 4-chloro-2-methoxyimino-3-oxobutyric acid obtained in step (II) above in one lot. The temperature of the reaction mass was maintained at −30° C. for 30 min. The progress of the reaction was monitored by HPLC. After completion of the reaction, the reaction mixture was poured into 200 ml chilled DM water and stirred for 1 hour at 25° C. The precipitated solid was filtered; washed with DM water until washings are neutral and dried to get the open chain condensed product. (Purity 99. 0%).

Step (IV)

Cyclisation with Thiourea

Tetrahydrofuran (50 ml) and water (50 ml) were charged into the reaction flask followed by the addition of condensed product (10.0 gm, 1.0 mol) obtained in step (III) above, thiourea(3.5 gm, 2.0 mol) and sodium acetate (15.7 gm, 5.0 mol). Stirred the reaction mixture at room temperature for 1 hr. The progress of the reaction was monitored by HPLC. After completion of reaction, the mixture was cooled to 10° C. and pH adjusted to 2.5 with 1:1 HCl. The mixture was stirred for 1 hour to complete precipitation. The precipitated solid was filtered, washed well with DM water until washings are neutral and dried under vacuum at 35° C. to yield Cefotaxime acid. (Purity: 92%).

EXAMPLE—6

Preparation of 7-[[(Z)-2-(aminothiazol-4-yl)-2-methoxyimino]acetamido]-3-(furanylcarbonyl) thiomethyl]-3-cephem-4-carboxylic Acid Sodium (Ceftiofur Sodium).

Step—I

Silylation of 7-amino-3-[(2-furanylcarbonyl)thiomethyl]-3-cephem-4-carboxylic Acid:

To a solution of 7-amino-3-[(2-furanylcarbonyl) thiomethyl]-3-cephem-4-carboxylic acid (6.8 gm, 1.2 mol) in ethyl acetate(68 ml), bis-silylated acetamide (BSA) (16.6 gm, 4.0 mol) was added drop wise at room temperature and continued stirring for 2–3 hrs at the same temperature.

Step (II)

Activation of 4-chloro-2-methoxyimino-3-oxobutyric Acid with $DMF/POCl_3$

To a suspension of vilsmeir reagent prepared from $POCl_3$ (3.58 gm, 1.4 mol) and DMF (1.71 gm, 1.4 mol) in acetonitrile (24 ml) was added 4-chloro-2-methoxyimino-3-oxobutyric acid (3.0 gm, 1.0 mol) obtained in example 1 or 2 under ice-cooling at 0–5° C. The mixture was stirred at the same temperature for 30 minutes.

Step—III

Condensation of Activated 4-chloro-2-methoxyimino-3-oxobutyric Acid and Silylated 7-amino-3-[(2-furanylcarbonyl)thiomethyl]-3-cephem-4-carboxylic Acid Silylated 7-amino-3-[(2-furanylcarbonyl)thiomethyl]-3-cephem-4-carboxylic acid obtained in step (I) above, was added to the activated acid solution obtained in step (II) above at −25° C. After being stirred at −28° C.~−10° C. for 1 hour, add ice-water (25 ml). The separated organic layer was washed with water (75 ml). The organic solution was dried and condensed under reduced pressure to give 5.0 gm of the required product.

Step (IV)

Cyclisation with Thiourea

Tetrahydrofuran (50 ml) and water (25 ml) were charged into the reaction flask followed by the addition of condensed product (5.0 gm) obtained in step (III) above, thiourea(0.9 gm) and sodium acetate (2.8 gm). Stirred the reaction mixture at room temperature for 3 hrs. The progress of the reaction was monitored by HPLC. After completion of reaction, sodium chloride (48.0 gm) was added to the reaction mixture and stirred at room temperature for 30 min. The tetrahydrofuran layer was separated and was added THF (80 ml), charcoal (0.5 gm) stirred for 1 hr at room temperature. To the THF layer $MgSO_4$ (5.0 gm) was added to remove the traces of water, decanted the THF layer, to which sodium-2-ethyl hexanoate (3.1 gm) in THF (20 ml) was added. Precipitation of the product started after 1 hr of stirring. The precipitated Ceftiofur sodium was filtered and washed with acetone (3.2 gm, Purity 98.0%).

EXAMPLE—7

Preparation of 7-[[(Z)-2-(aminothiazol-4-yl)-2-methoxyimino]acetamido]-3-(furanylcarbonyl) thiomethyl]-3-cephem-4-carboxylic Acid Sodium (Ceftiofur Sodium).

Step (I)

Synthesis of diethyl-(4-chloro-2-methoxyimino-3-oxabutrate) Phosphoridate 4-chloro-2-methoxyimino-3-oxobutyric acid (3.0 gm) obtained in example 1 or 2 was suspended in dichloromethane (24 ml). Triethylamine (0.90 gm) was added into this solution and then diethylchlorophosphoridate (24.52 gm) was also added thereto over 20 minutes while maintaining the solution under nitrogen atmosphere at 0° C. to 5° C. The mixture was stirred for 2 hours. After the reaction was completed, distilled water (25 ml) was added to the reaction solution and the mixture was stirred for 5 minutes.

The organic layer was separated, washed successively with 5% aqueous sodium bicarbonate solution (25 ml) and saturated saline (25 ml), dried over magnesium sulfate, filtered and then concentrated under reduced pressure to obtain 5.9 gm of the title compound.

Step—II
Silylation of 7-amino-3-[(2-furanylcarbonyl)thiomethyl]-3-cephem-4-carboxylic Acid:

To a solution of 7-amino-3-[(2-furanylcarbonyl)thiomethyl]-3-cephem-4-carboxylic acid (6.8 gm, 1.2 mol) in ethyl acetate(68 ml) N,O-bis-(trimethylsilyl)acetamide (BSA) (16.6 gm, 4.0 mol) was added drop wise at room temperature and continued stirring for 2–3 hrs at the same temperature.

Step—III
Condensation of diethyl-(4-chloro-2-methoxyimino-3-oxabutrate) Phosphoridate and Silylated 7-amino-3-[(2-furanylcarbonyl)thiomethyl]-3-cephem-4-carboxylic Acid The suspension of the activated reagent obtained in step (I) above was added to the silylated 7-amino-3-[(2-furanylcarbonyl)thiomethyl]-3-cephem-4-carboxylic acid obtained in step (II) above at −25° C. After stirring for 1 hour at −30° C. to −10° C., ice-water (25 ml) was added. The separated organic layer was washed with water (75 ml). The organic solution was dried and condensed under reduced pressure to give 7.5 gm of the required product.

Step (IV)
Cyclisation with Thiourea

Tetrahydrofuran (50 ml) and water (25 ml) were charged into the reaction flask followed by the addition of condensed product (5.0 gm) obtained in step (III) above, thiourea (0.9 gm) and sodium acetate (2.8 gm). Stirred the reaction mixture at room temperature for 3 hrs. The progress of the reaction was monitored by HPLC. After completion of reaction, sodium chloride (48.0 gm) was added to the reaction mixture and stirred at room temperature for 30 min. The tetrahydrofuran layer was separated and was added THF (80 ml), charcoal (0.5 gm) stirred for 1 hr at room temperature. To the THF layer MgSO$_4$ (5.0 gm) was added to remove the traces of water, decanted the THF layer, to which sodium-2-ethyl hexanoate (3.1 gm) in THF (20 ml) was added. Precipitation of the product started after 1 hr of stirring. The precipitated Ceftiofur sodium was filtered and washed with acetone (3.0–3.2 gm, Purity 98.0%).

What is claimed is:
1. A process for the preparation of a cephalosporin antibiotic of the formula (II)

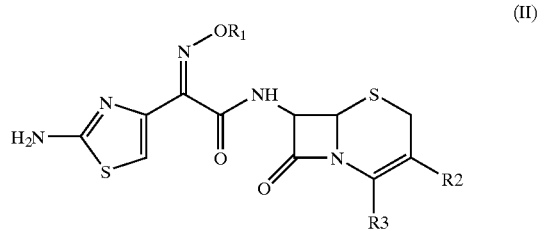
(II)

wherein $R_1$ represents $CH_3$, $CR^aR^bCOOR^c$ where $R^a$ and $R^b$ independently represent hydrogen or methyl and $R^c$ represents hydrogen or ($C_1$–$C_3$)alkyl; $R_2$ represents H, $CH_3$, $CH_2OCH_3$, $CH_2OCOCH_3$, $CH=CH_2$,

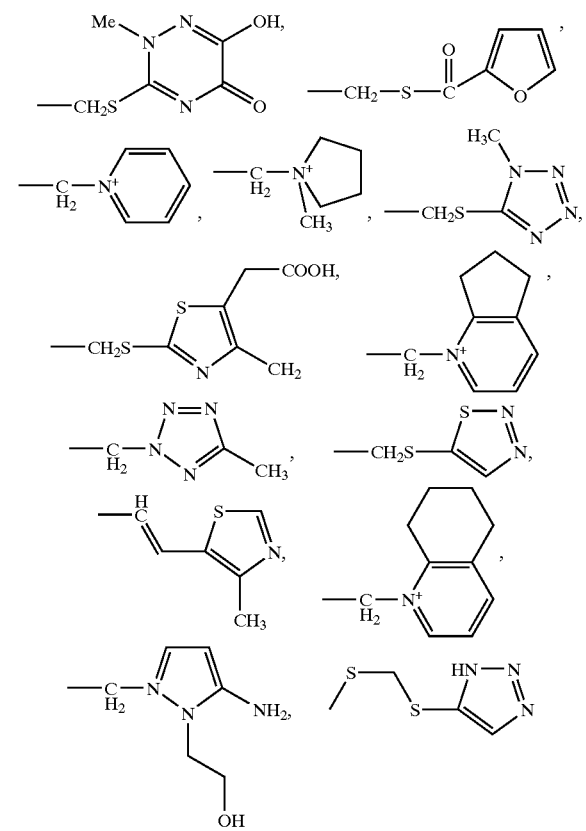

and $R_3$ is carboxylate ion or $COOR^d$, where $R^d$ is selected from the group consisting of hydrogen, esters which form a prodrug and a counter ion which forms a salt, said process comprising:
 (i) hydrolyzing and halogenating of the ester of formula (III)

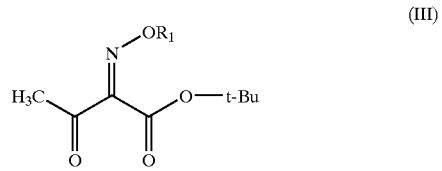
(III)

by photochemical irradiation in one pot using a halogenating agent in the absence or presence of a solvent at a temperature in a range of −20° C. to 30 ° C., to produce compound of formula (I)

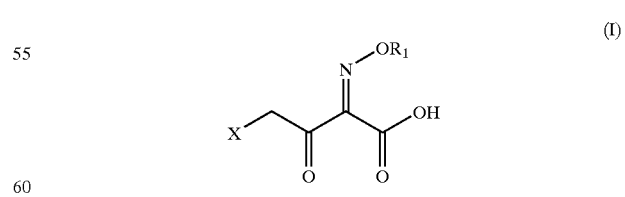
(I)

wherein $R_1$ represents $CH_3$, $CR^aR^bCOOR^c$ where $R^a$ and $R^b$ independently represent hydrogen or methyl and $R^c$ represents hydrogen or ($C_1$–$C_3$)alkyl, and X represents halogen such as chlorine or bromine,
 (ii) activating the 4-halogeno2-substitutedimino-3-oxo-butyric acid of formula (I) using conventional activation agents in the presence of a solvent at a temperature in a range of −50° C. to 10° C. to produce a compound of formula (IV)

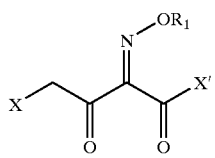

(IV)

wherein X and $R_1$ are as defined earlier and X' represents a halogen or activating group, (iii) condensing the activated compound of the formula (IV) with a 7-amino cephem derivative of formula (V)

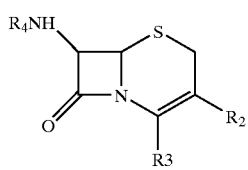

(V)

wherein $R_4$ is hydrogen or trimethylsilyl, and $R_2$ and $R_3$ are as defined above in the presence of a solvent at a temperature in a range of −50° C. to 10° C. to produce a compound of formula (VI)

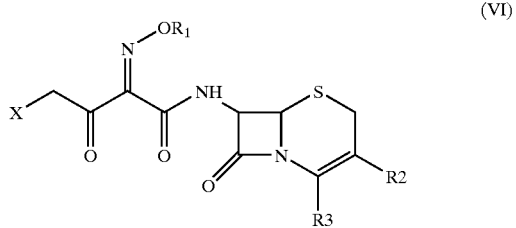

(VI)

where all symbols are as defined above, (iv) cyclizig of the compound of formula (VI) with thiourea in the presence of water miscible solvents at room temperature to produce the cephalosporin antibiotic of the formula (II) where all symbols are as defined earlier, (v) optionally converting the compound of formula (II) to its pharmaceutically-acceptable salt.

2. The process according to claim 1, wherein the solvent used in step (i) is selected from the group consisting of diisopropyl ether, dichloromethane, acetic acid and mixtures thereof.

3. The process according to claim 1, wherein the halogenating agent used is chlorine or bromine.

4. The process according to claim 1, wherein the light source used for photochemical halogenation is IR or UV radiation.

5. The process according to claim 1, wherein the activation in step (ii) is carried out using $PCl_5$, $DMF/POCl_3$, oxalyl chloride, $SOCl_2/DMF$, diphenylchlorophosphoridate or dialkyl chlorophosphoridate.

6. The process according to claim 1, wherein solvent used in step (ii) is selected from the group consisting of halogenated alkanes, ethyl acetate, tetrahydrofuran, aromatic hydrocarbons, acetone, acetonitrile, dialkylethers and mixtures thereof.

7. The process according to claim 1, wherein the solvent used in step (iii) is selected from the group consisting of halogenated alkanes, ethyl acetate, tetrahydrofuran, aromatic hydrocarbons, acetone, acetonitrile, dialkylethers and mixtures thereof.

8. The process according to claim 1, wherein the cyclizing in step (iv) is carried out using a mixture of water and an organic solvent selected from the group consisting of tetrahydrofuran, acetone, acetonitrile, N,N-dimethylformamide, N,N-dimethylacetamide, dioxane, $(C_1–C_3)$alcohol and mixtures thereof, in the presence of sodium acetate.

9. The process according to claim 1, wherein the $R_d$ is a counter ion, and wherein the counter ion is an alkali metal.

10. The process according to claim 9, wherein the alkali metal is sodium.

11. The process according to claim 1, wherein the $R_d$ is a prodrug ester, and wherein the prodrug ester is —$(CH_2)$—O—C(=O)—C$(CH_3)_3$, —CH$(CH_3)$—O—C(=O)—$CH_3$ or —CH$(CH_3)$—O—C(=O)—O—CH$(CH_3)_2$.

12. The process according to claim 1, wherein the compound of formula (I) obtained is a syn-isomer.

13. The process according to claim 1, wherein the compound of the formula (VI) is cyclized with thiourea without isolating the condensed product.

14. The process according to claim 1, wherein X' represents chlorine or bromine or activating groups selected from

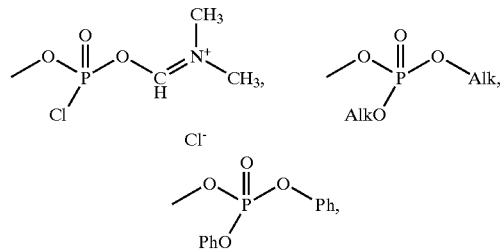

where the Alk group represents a $(C_1–C_4)$alkyl group.

15. The process according to claim 14, wherein Alk group represents a $(C_1–C_4)$alkyl group selected from the groups consisting of methyl, ethyl, n-propyl, iso-propyl, n-butyl and iso-butyl.

* * * * *